United States Patent [19]

Kachholz et al.

[11] Patent Number: 4,614,717

[45] Date of Patent: Sep. 30, 1986

[54] PROCESS FOR CULTIVATION OF ORGANISMS WHEREIN A UNIFORM PROTEIN FROM MICROORGANISMS IS ENZYMATICALLY DEGRADED

[75] Inventors: Traudel Kachholz, Kronberg; Udo Scharf, Kelkheim; Merten Schlingmann, Königstein, all of Fed. Rep. of Germany

[73] Assignee: Hoechst Aktiengesellschaft, Fed. Rep. of Germany

[21] Appl. No.: 706,519

[22] Filed: Feb. 28, 1985

Related U.S. Application Data

[62] Division of Ser. No. 599,159, Apr. 11, 1984, abandoned.

[30] Foreign Application Priority Data

Apr. 13, 1983 [DE] Fed. Rep. of Germany ....... 3313330

[51] Int. Cl.$^4$ .............................................. C12P 21/06
[52] U.S. Cl. ........................................ 435/69; 435/68; 435/70; 435/169; 435/253; 435/804; 435/822; 530/825
[58] Field of Search ............... 260/112 R; 435/68, 69, 435/70, 169, 253, 804, 822

[56] References Cited

U.S. PATENT DOCUMENTS

| 3,135,663 | 6/1964 | Muggleton et al. ............... 435/253 |
| 3,360,440 | 12/1967 | Haab et al. ..................... 435/253 X |
| 3,399,115 | 8/1968 | Sellers, Jr. ..................... 435/253 X |
| 3,434,928 | 3/1969 | Naito et al. ..................... 435/253 X |
| 3,888,837 | 6/1975 | Tsumita et al. .................. 435/70 X |
| 3,932,671 | 1/1976 | Yokotsuka et al. ............... 435/69 X |
| 4,166,004 | 8/1979 | Präve et al. ..................... 435/253 |
| 4,186,188 | 1/1980 | Gumprecht .............. 260/112 R X |
| 4,206,243 | 6/1980 | Schlingmann et al. .... 260/112 R X |
| 4,427,658 | 1/1984 | Maubois et al. ................. 435/69 X |
| 4,443,540 | 4/1984 | Chervan et al. ..................... 435/69 |
| 4,452,888 | 6/1984 | Yamazaki et al. ............. 260/112 R |
| 4,559,307 | 12/1985 | Hopkins ......................... 435/69 X |

FOREIGN PATENT DOCUMENTS

| 79023 | 11/1982 | European Pat. Off. . |
| 1568432 | 1/1968 | France . |
| 1221427 | 2/1971 | United Kingdom . |
| 2043651 | 11/1980 | United Kingdom . |
| 2077760 | 12/1981 | United Kingdom ............... 435/253 |
| 649745 | 6/1979 | U.S.S.R. . |

OTHER PUBLICATIONS

Difco Manual of Dehydrated Culture Media and Reagents, 9th Edition, Difco Laboratories, Inc., Detroit, Mich.
European Patent Office Search Report EP 84 10 3927.
Chem. Abstracts, vol. 99, 1983, 21162p, Scharf et al, effective date–May 11, 1983.

*Primary Examiner*—Howard E. Schain
*Attorney, Agent, or Firm*—Finnegan, Henderson, Farabow, Garrett & Dunner

[57] ABSTRACT

Products which are soluble without opalescence even at pH 3 and which, because of their reproducible composition, are particularly well suited as a source of nitrogen for organisms are obtained by enzymatic degradation of uniform microbial cell aggregates, using endoproteases, and isolation of the protein fraction up to 2,000 Dalton, preferably from 400 to 1,500 Dalton.

42 Claims, No Drawings

PROCESS FOR CULTIVATION OF ORGANISMS WHEREIN A UNIFORM PROTEIN FROM MICROORGANISMS IS ENZYMATICALLY DEGRADED

This is a division of application Ser. No. 599,159 filed Apr. 11, 1984, now abandoned.

Protein hydrolyzates which are obtained by enzymatic hydrolysis of proteins from meat, milk or soybeans are marketed under the name "peptone". These peptones must fulfil a number of requirements: thus, no opalescence should appear in the weakly acid range (pH 4), no precipitation should occur on heating in an autoclave (121° C. under 1 bar gage pressure), no foaming should be produced in vigorously agitated fermenters, and the molecular weight must be in a range favorable for microbial growth.

Due to the source of the protein, the composition of these peptones varies within certain limits, and this makes elaborate standardization necessary, not only for scientific uses but especially also for industrial uses. It has now been found that enzymatic hydrolyzates of defined microbial proteins do not exhibit this disadvantage.

Thus the invention relates to a source of nitrogen for organisms which is composed of an enzymatic hydrolyzate of a microbial protein having a molecular weight of up to 2,000, preferably from 400 to 1,500, Dalton or which contains a product of this type.

These hydrolyzates dissolve in water to give clear solutions, exhibit no opalescence even at pH 3, and also fulfil the abovementioned requirements in respect of heating in an autoclave and foaming in vigorously agitated fermenters. In addition, it has emerged that these hydrolyzates are source of nitrogen which are at least comparable with peptones based on meat and casein, and in many cases they are even superior. In every case, the hydrolyzates according to the invention have a uniform, reproducible composition, and thus they have a defined content of nitrogen and aminoacids, since they are derived from a uniform source of protein.

The products according to the invention are prepared by enzymatic degradation of uniform microbial cell aggregates using endoproteases, and by isolation of the protein fractions in the range of molecular weight up to 2,000, preferably of 400 to 1,500, Dalton. The conditions for this process primarily depend on whether the main aim is the preparation of the sources of nitrogen for organisms, according to the invention, or whether this preparation is integrated in the working-up of microbial proteins for other purposes, especially for human nutrition. Obviously, in the latter case care has to be taken that the enzymatic degradation does not result in by-products, such as bitter substances, which would make the other fractions, especially the higher molecular weight fraction or fractions, unsuitable for use for human nutrition.

If the preparation of the sources of nitrogen according to the invention is the main aim, during the enzymatic degradation the higher molecular weight fractions will accordingly be returned, continuously or batchwise, to the enzymatic hydrolysis, and thus the proportion of the required low molecular weight fraction will be correspondingly raised. If the intention is that the higher molecular weight fractions will be utilized elsewhere, for example their use as foodstuff additives according to German Offenlegungsschrift No. 3,143,947, especially as emulsifiers, then this return of the product to the hydrolysis step will be wholly or partly dispensed with.

The enzymatic degradation of proteins, including those of microbial origin, is known, as is the separation into fractions by molecular weight. Advantageous process conditions are described in the abovementioned German Offenlegungsschrift.

Preferably, an aqueous suspension of the microbial protein is homogenized, adjusted to a pH suitable for the enzyme and, with stirring, brought to the optimal temperature for the enzyme employed. After addition of the enzyme, thorough mixing of the suspension is continued and it is exposed to the action of the enzyme until the required degradation has taken place. The enzyme is then inactivated in a known manner, generally by heating, for example by passing in steam.

The separation of the protein mixture thus obtained is carried out by customary processes, advantageously by membrane separation processes, especially ultrafiltration. Membrane separating processes are generally used, especially in biotechnology (review article: H. Strathmann, Chemie-Technik 11 (1982) 813-819). For the preparation of the products according to the invention, ultrafiltration in sheet, tube, capillary tube, coiled membrane and, especially, hollow fiber apparatus is preferred. Particularly suitable processes are likewise described in the abovementioned German Offenlegungsschrift.

An advantageous embodiment of the invention takes the form of degrading, in a first step, the microbial protein with trypsin, the enzyme:substrate weight ratio which is observed being about 1:500. After separating out the higher molecular weight fractions by hollow fiber ultrafiltration (exclusion limit 100,000 Dalton), the permeate is treated with alkalase, the enzyme:substrate weight ratio which is observed being about 1:50. In this case, the retentate (concentrate) is utilized elsewhere.

In another embodiment of the invention, the two enzymes mentioned are employed at the same time in the weight ratio indicated, and the degradation process is carried out in one step or in two steps.

Moreover, continuous hydrolysis is particularly advantageous, the hydrolyzate being recycled via an ultrafiltration apparatus, and the retentate being continuously returned to the hydrolysis.

In principle, all microbial cell aggregates which are produced industrially and the resulting composition of which is uniform are suitable as the starting material. Methylotrophic, especially obligate methylotrophic, organisms are preferred, especially microorganisms utilizing methanol, since methanol is a low-cost source of carbon which is not dependent on petroleum. Large numbers of microorganisms utilizing methanol are known and they are described in, for example, European Patent Application Nos. 35,831 and 37,273, in German Auslegeschrift No. 2,161,164 and, especially, in German Pat. No. 2,633,451.

Microorganisms contain, as do all cells, not only proteins and carbohydrates but also nucleic acids and lipids. During the working up of microbial cell aggregates to obtain proteins for human nutrition, both the nucleic acids and the lipids are separated out, since they adversely affect the odor, flavor and storage stability of the proteins. The lipids are removed by extraction with lipid solvents. Appropriate processes are mentioned in, for example, German Pat. No. 2,633,666. The process claimed in this German patent is particularly preferred, this entailing the lipids being extracted using an extraction mixture comprising ammonia and a polar solvent from the series of lower alkanols, lower glycols or the methyl or ethyl ethers of a lower glycol, and this extraction mixture containing not more than 30% by weight of water relative to the amount of solvent employed. The preferred solvent is methanol. The ammonia content is preferably 1 to 10% by weight relative to the amount of solvent employed. This is followed by one-step or multi-step extraction of the nucleic acids, using water.

It is advantageous, before extracting the lipids, to subject the microbial cell aggregates to heat treatment at temperatures from 105° to 160° C. This heat treatment advantageously lasts 3 to 40, especially 5 to 20, minutes at a product temperature of 105° to 140° C. German Patent Application P No. 3,308,024.0 relates to a process of this type; it not only leads to an improvement in the mechanical properties of the crude microbial biomass, which results in the loss of protein in the subsequent extraction being lower, but it also has an advantageous effect on the physiological properties of the proteins.

A bacterial aggregate from Methylomonas clara ATCC 31 226 according to German Pat. No. 2,633,451 (U.S. Pat. No. 4,166,004), Example 2, with a nucleic acid content of 8–10%, a crude fat content of 5 to 10% and a residual moisture content of 2 to 2 to 4% was employed for the examples which follow. This material was treated in a fluidized bed at an air temperature of 160° C. for 30 minutes, a product temperature of 120° C. being maintained for 10 minutes. This cell aggregate which had undergone heat treatment was then extracted, in accordance with Example 1 of German Pat. No. 2,633,666 (U.S. Pat. No. 4,206,243), with methanolic ammonia and then with water. Here and in the following text, percentage data relate to weight.

EXAMPLE 1

A starting material which has been extracted once with water and has a residual nucleic acid content of 3 to 5% is diluted to a solids content of 5%, the pH is adjusted to 8.0 with dilute sodium hydroxide solution, and the mixture is heated to 50° C. 0.1 g of trypsin PTN 3.0 S and 1 g of alkalase 0.6 L are added per liter of suspension, and the mixture is stirred for 2 hours, during which the temperature and pH are maintained constant, the latter by addition of dilute sodium hydroxide solution. The same amounts of the said enzymes are now added once more, and the pH and temperature are maintained for a further 2 hours with stirring.

The enzymes are inactivated by heating to 80° C., and the hydrolyzate is fractionated by recycling through a hollow fiber ultrafiltration apparatus (Romicon PM 100) at a flow rate of 6,000 liters per hour under 1.8 bar, drawing off 500 to 250 liters of permeate per hour. The retentate which does not pass through the membrane is returned to the reactor, and the permeate which is drawn off is concentrated to 20% dry matter in a falling film evaporator and is spray-dried. About 60% of peptone which is soluble in water to give a clear solution, and which shows no opalescence at pH 3, are obtained.

EXAMPLE 2

A starting material which has been extracted twice with water and has a residual nucleic acid content of 2% is diluted to a solids content of 10%, the pH is adjusted to 8.0 with dilute sodium hydroxide solution, and the suspension is heated to 50° C. Then 0.2 g of trypsin PTN 3.0 S is added per liter, and the mixture is stirred for 4 hours, maintaining the temperature and the pH (by addition of dilute sodium hydroxide solution) constant. The mixture is heated to 80° C. to inactivate the enzyme, and the hydrolyzate is recycled through the hollow fiber ultrafiltration apparatus mentioned in Example 1. The retentate which does not pass through the membrane after the hydrolyzate has flowed through several times is spray-dried and used as a foodstuffs additive.

1/50 of the weight of solids in the permeate of alkalase 0.6 L is added to the permeate, and it is again incubated at 50° C. for 4 hours. The alkalase is then inactivated by heating to 80° C. The hydrolyzate is concentrated to 20% dry matter in a falling film evaporator and is spray-dried. The amount of peptone obtained is about 30% of the weight of solids employed.

Table 1 below shows further examples of hydrolysis procedures. The process used was that in Example 2 with the modifications mentioned in the table.

TABLE 1

| Example | Substrate concentration, % | Enzyme | Ratio* | % yield of permeate |
|---|---|---|---|---|
| 3 | 2 | Trypsin PTN 3.0 S | 100 | 77.1 |
|   |   | Alkalase 0.6 L | 10 |   |
| 4 | 10. | Trypsin PTN 3.0 S | 500 | 55.7 |
|   |   | Pronase E | 1000 |   |
| 5 | 5 | Trypsin PTN 3.0 S | 50 | 72.2 |
|   |   | Alkalase 0.6 L | 5 |   |

*Substrate/enzyme weight ratio

The peptone obtained by Example 1 was compared with casein and meat peptones by incorporation into nutrient media of the following compositions:

TABLE 2

| Nutrient media for (in g/l of distilled water) | | | | | |
|---|---|---|---|---|---|
| Lactobacilli Brevibacterium Corynebacterium Propionibacterium | | Other bacteria | | Yeasts and mould fungi | |
| Meat extract | 5.0 | Meat extract | 5.0 | Malt extract | 30.0 |
| Yeast extract | 5.0 | Na$_2$HPO$_4$ | 2.0 | Peptone | 3.0 |
| Glucose | 20.0 | NaCl | 3.0 |   |   |
| K$_2$HPO$_4$ | 2.0 | Peptone | 10.0 |   |   |
| (NH$_4$)$_2$H citrate | 2.0 |   |   |   |   |
| CH$_3$COONa | 5.0 |   |   |   |   |
| MgSO$_4$ | 0.1 |   |   |   |   |
| MnSO$_4$ | 0.05 |   |   |   |   |
| Peptone | 10.0 | pH | 7.0 | pH | 5.5 |
| pH | 7.0 |   |   |   |   |

The microorganisms mentioned in Table 3 below were cultured on these nutrient media:

TABLE 3

| | Growth on: (O.D./30 ml) | | | | | | | | | | | | | | |
|---|---|---|---|---|---|---|---|---|---|---|---|---|---|---|---|
| | Peptone according to invention | | | | | Meat peptone | | | | | Casein peptone | | | | |
| Organism | 1 d | 2 d | 3 d | 4 d | 5 d | 1 d | 2 d | 3 d | 4 d | 5 d | 1 d | 2 d | 3 d | 4 d | 5 d |

TABLE 3-continued

| | | | | | | | | | | | | | | |
|---|---|---|---|---|---|---|---|---|---|---|---|---|---|---|
| Rhodococcus erythropolis | 14.5 | 14.5 | 17.0 | 16.5 | 15.5 | 10.0 | 13.5 | 13.0 | 13.5 | 12.0 | 8.5 | 13.0 | 12.0 | 13.5 | 17.0 |
| Micrococcus caseolyticus | 1.0 | 0.5 | 1.5 | 1.0 | 0.8 | 0.5 | 1.0 | 3.0 | 2.0 | 0.7 | 2.0 | 2.5 | 2.5 | 2.0 | 1.5 |
| Bacillus licheniformis | 6.0 | 10.0 | 12.5 | 11.0 | 9.35 | 9.5 | 7.5 | 11.5 | 10.5 | 8.4 | 9.0 | 6.5 | 6.0 | 7.5 | 6.5 |
| Escherichia coli | — | 2.02 | 1.92 | 1.97 | 2.25 | — | 1.82 | 1.53 | 1.78 | 2.57 | — | 1.29 | 1.32 | 1.20 | 1.21 |
| Klebsiella pneumoniae | — | 3.58 | 4.04 | 3.97 | 3.93 | — | 1.40 | 1.15 | 1.24 | 1.76 | — | 2.79 | 2.83 | 2.87 | 1.24 |
| Pseudomonas aeruginosa | — | 1.82 | 1.97 | 1.95 | 2.56 | — | 2.44 | 1.89 | 2.59 | 3.9 | — | 1.91 | 2.08 | 2.08 | 3.27 |
| Lactobacillus buchneri | 5.0 | 8.6 | 5.4 | 5.7 | 6.3 | 7.4 | 13.8 | 6.6 | 5.9 | 5.1 | 6.8 | 7.8 | 6.5 | 15.9 | 5.6 |
| Brevibacterium linens | 5.2 | 7.2 | 8.4 | 8.0 | 8.4 | 0.6 | 6.0 | 6.8 | 7.1 | 6.8 | 0.8 | 7.6 | 7.4 | 6.9 | 6.2 |
| Leuconestoc cremoris | 5.4 | 5.8 | 6.2 | 5.4 | 5.4 | 5.2 | 5.8 | 5.4 | 5.0 | 4.9 | 4.6 | 5.2 | 4.6 | 4.6 | 4.7 |
| Debaryomyces hansenii | 2.8 | 19.6 | 28.5 | 37.5 | 40.0 | 2.5 | 11.0 | 24.0 | 25.0 | 28.0 | 2.2 | 10.4 | 11.0 | 15.0 | 14.0 |
| Kluyveromyces fragilis | 6.9 | 3.4 | 10.0 | 10.0 | 11.0 | 3.9 | 3.8 | 10.0 | 11.0 | 12.0 | 3.7 | 6.8 | 13.5 | — | 11.0 |
| Candida rugosa | 6.8 | 6.6 | 8.0 | 8.0 | 7.0 | 7.0 | 5.4 | 10.5 | 9.0 | 7.5 | 6.4 | 7.0 | 8.5 | 8.0 | 9.0 |
| Hansenula subpelliculosa | 12.5 | 35.6 | 46.5 | 60.0 | 67.0 | 12.3 | 29.6 | 47.0 | 64.0 | 60.0 | 16.5 | 33.2 | 48.5 | 52.0 | 53.0 |
| Saccharomyces cerevisiae | 6.4 | 10.6 | 25.0 | 24.0 | 25.0 | 9.2 | 11.0 | 24.5 | 26.0 | 26.0 | 9.5 | 20.4 | 22.5 | 28.0 | 34.0 |

| | Growth on: (Dry weight /100 ml) | | | | | | | | | | | |
|---|---|---|---|---|---|---|---|---|---|---|---|---|
| | Peptone according to invention | | | | Meat peptone | | | | Casein peptone | | | |
| Organism | 2 d | 4 d | 6 d | 8 d | 2 d | 4 d | 6 d | 8 d | 2 d | 4 d | 6 d | 8 d |
| Aspergillus tamarii | 0.78 | 0.79 | 0.82 | 0.50 | 0.51 | 0.074 | 0.83 | 0.84 | 1.05 | 0.92 | 0.80 | 0.70 |
| Penicillium camembertii | 0.03 | 0.03 | 0.06 | 0.10 | 0.03 | 0.02 | 0.05 | 0.08 | 0.03 | 0.04 | 0.05 | 0.07 |
| Rhizopus oryzae | 0.37 | 0.48 | 0.53 | 0.51 | 0.40 | 0.32 | 0.57 | 0.59 | 0.45 | 0.62 | 0.57 | 0.57 |
| Stereum hirsutum | 0.03 | 0.05 | 0.17 | 0.74 | 0.05 | 0.07 | 0.15 | 0.19 | 0.04 | 0.07 | 0.33 | 0.47 |

We claim:

1. A process for cultivation of organisms, wherein a uniform protein from a microorganism is subjected to enzymatic degradation and to separation of the fraction up to 2000 dalton, which is then utilized as a peptone in said cultivation of organisms.

2. A process as claimed in claim 1, wherein the protein is from a methylotrophic microorganism.

3. A process as claimed in claim 1, wherein the protein is from an obligate methylotrophic microorganism.

4. A process as claimed in claim 1, wherein the protein is from a Methylomonas clara ATCC 31 226.

5. A process as claimed in claim 1, wherein the protein is from a methanol utilizing microorganism.

6. A process as claimed in claim 2, wherein the protein is from a methanol utilizing microorganism.

7. A process as claimed in claim 3, wherein the protein is from a methanol utilizing microorganism.

8. A process as claimed in claim 1, wherein the protein fraction of 400 to 1500 dalton is separated.

9. A process as claimed in claim 2, wherein the protein fraction of 400 to 1500 dalton is separated.

10. A process as claimed in claim 3, wherein the protein fraction of 400 to 1500 dalton is separated.

11. A process as claimed in claim 4, wherein the protein fraction of 400 to 1500 dalton is separated.

12. A process as claimed in claim 5, wherein the protein fraction of 400 to 1500 dalton is separated.

13. A process according to claim 6, wherein the protein fraction of 400 to 1500 dalton is separated.

14. A process as claimed in claim 7, wherein the protein fraction of 400 to 1500 dalton is separated.

15. A process as claimed in claim 1, wherein the separation of the wanted fraction is achieved by membrane separation.

16. A process as claimed in claim 2, wherein the separation of the wanted fraction is achieved by membrane separation.

17. A process as claimed in claim 3, wherein the separation of the wanted fraction is achieved by membrane separation.

18. A process as claimed in claim 4, wherein the separation of the wanted fraction is achieved by membrane separation.

19. A process as claimed in claim 5, wherein the separation of the wanted fraction is achieved by membrane separation.

20. A process as claimed in claim 6, wherein the separation of the wanted fraction is achieved by membrane separation.

21. A process as claimed in claim 7, wherein the separation of the wanted fraction is achieved by membrane separation.

22. A process as claimed in claim 8, wherein the separation of the wanted fraction is achieved by membrane separation.

23. A process as claimed in claim 9, wherein the separation of the wanted fraction is achieved by membrane separation.

24. A process as claimed in claim 10, wherein the separation of the wanted fraction is achieved by membrane separation.

25. A process as claimed in claim 11, wherein the separation of the wanted fraction is achieved by membrane separation.

26. A process as claimed in claim 12, wherein the separation of the wanted fraction is achieved by membrane separation.

27. A process as claimed in claim 17, wherein the separation of the wanted fraction is achieved by membrane separation.

28. A process as claimed in claim 14, wherein the separation of the wanted fraction is achieved by membrane separation.

29. A process as claimed in claim 15, wherein ultrafiltration is the separation process.

30. A process as claimed in claim 16, wherein ultrafiltration is the separation process.

31. A process as claimed in claim 17, wherein ultrafiltration is the separation process.

32. A process as claimed in claim 18, wherein ultrafiltration is the separation process.

33. A process as claimed in claim 19, wherein ultrafiltration is the separation process.

34. A process as claimed in claim 20, wherein ultrafiltration is the separation process.

35. A process as claimed in claim 21, wherein ultrafiltration is the separation process.

36. A process as claimed in claim 22, wherein ultrafiltration is the separation process.

37. A process as claimed in claim 23, wherein ultrafiltration is the separation process.

38. A process as claimed in claim 24, wherein ultrafiltration is the separation process.

39. A process as claimed in claim 25, wherein ultrafiltration is the separation process.

40. A process as claimed in claim 26, wherein ultrafiltration is the separation process.

41. A process as claimed in claim 27, wherein ultrafiltration is the separation process.

42. A process as claimed in claim 28, wherein ultrafiltration is the separation process.

* * * * *